United States Patent [19]

Haas et al.

[11] 4,100,088
[45] Jul. 11, 1978

[54] IMAGING COMPOSITION

[75] Inventors: Werner E. L. Haas, Webster; Gary A. Dir, Fairport, both of N.Y.

[73] Assignee: Xerox Corporation, Stamford, Conn.

[21] Appl. No.: 702,362

[22] Filed: Jul. 2, 1976

[51] Int. Cl.² ............................................. G01N 27/00
[52] U.S. Cl. .............................. 252/62.52; 252/62.55
[58] Field of Search ........................ 252/62.52, 62.55

[56] References Cited

U.S. PATENT DOCUMENTS

| | | | |
|---|---|---|---|
| 3,597,356 | 8/1971 | Diperstein et al. | 252/62.52 |
| 3,764,540 | 10/1973 | Khalafalla et al. | 252/62.55 |
| 3,786,346 | 1/1974 | Lorenzi | 252/62.52 X |
| 3,981,844 | 9/1976 | Romankiw | 252/62.52 |

FOREIGN PATENT DOCUMENTS

| | | | |
|---|---|---|---|
| 987,487 | 4/1976 | Canada | 252/62.54 |
| 705,050 | 3/1954 | United Kingdom | 252/62.52 |

*Primary Examiner*—F.C. Edmundson
*Attorney, Agent, or Firm*—James J. Ralabate; George J. Cannon; John E. Beck

[57] ABSTRACT

A composition responsive to magnetic fields and comprising a ferrofluid and metal flakes. The metal flakes align with the ferrofluid in response to magnetic lines of force and along the magnetic lines of force. Excellent contrast is provided between portions of the composition wherein the metal flakes are seen along edges or ends and portions of the composition wherein the broad surface area of the flakes are presented to view.

9 Claims, No Drawings

IMAGING COMPOSITION

BACKGROUND OF THE INVENTION

This invention relates to magnetically responsive imaging compositions; and, more particularly, to compositions comprising a ferrofluid.

There has recently been introduced an magnetic imaging system which employs a latent magnetic image on a magnetizable recording medium which can then be utilized for purposes such as electronic transmission or in a duplicating process by repetitive toning or transfer of the developed image. Such latent magnetic image is provided by any suitable magnetization procedure whereby a magnetized layer of marking material is magnetized and such magnetism transferred imagewise to the magnetic substrate. Such a process is more fully described in U.S. Pat. No. 3,804,511 to Rate et al.

The latent magnetic image, by way of analogy to xerographic imaging, is developed with a magnetic developer to render the latent magnetic image visible. The developed, visible, magnetic image is then typically transferred to a receiver such as, for example, a sheet of paper to produce a final copy or print. This final copy or print is typically referred to as hard copy.

Concurrently with the growth of interest in magnetic imaging, there has been a growth of interest in magnetic developers to render the latent magnetic images visible.

For example, U.S. Pat. No. 3,221,315 to Brown et al. is directed to the utilization of encapsulated ferrofluids in a magnetic recording medium wherein the ferrofluid orientation in the presence of a magnetic field exhibits a variable light-responsive characteristic. In this case, the magnetic recording medium is self-developing in the sense that magnetic marking material need not be employed to present a visible image. In other situations, latent magnetic images are rendered visible by magnetic marking material. For example, U.S. Pat. No. 3,627,682 to Hall et al. is directed to binary toners for developing latent magnetic images. These binary toners include a particulate hard magnetic material and a particulate soft magnetic material in each toner particle. The toner particle includes these two materials and a binder material. For dry development, the toner particles are mechanically mixed with polystyrene beads to form a two component developer.

In addition to magnetic marking material being applied directly to the latent magnetic image, there is also interest in novel compositons and techniques useful for rendering latent magnetic images visible. For example, U.S. Pat. No. 3,013,206 to Youngquist et al. discloses a magnetic reader comprising a hollow non-ferromagnetic vessel having a cavity field with a suspension of flat, visible, weakly ferromagnetic crystals which orient when suspended in the liquid and in response to a magnetic field.

SUMMARY OF THE INVENTION

It is, therefore, an object of this invention to provide a novel imaging composition.

It is another object of this invention to provide a novel imaging composition responsive to magnetic fields.

It is a further object of this invention to provide a novel composition responsive to magnetic fields, the response to which is easily visibly detectable.

The foregoing objects and others are accomplished in accordance with this invention by forming a composition comprising a ferrofluid and metal flakes. The composition can be readily fabricated by adding metal flakes such as, for example, aluminum flakes, to a ferrofluid which can be either water based or hydrocarbon based. Optionally, a compatible diluent can be added to comprise up to about 98.5 percent by weight of the resulting composition in some embodiments and these compositions still exhibit satisfactory contrast when subjected to the influence of a magnetic field.

DETAILED DESCRIPTION OF THE PREFERRED EMBODIMENTS

"Ferrofluids" as used herein means stable colloidal dispersions of ferri- or ferro-magnetic particles in a liquid medium. The liquid medium can be either water or a hydrocarbon liquid medium. The ferri- or ferro-magnetic particles do not flocculate or settle out under the influence of either gravatational or magnetic fields. Ferrofluids behave much like their liquid vehicle in the absence of a magnetic field; however, when a field is applied, the colloidal particles carry their surfactant coating in a substantial solvation sheath along the field gradient. Typically, the surfactant employed is a long-chain organic acid such as oleic acid, linoleic acid; succinic acid derivatives; ECA 3852 manufactured by Exxon Corporation. The particles are less than a critical size to be colloidally stable and in order that the energy of domain wall formation be greater than the energy for rotation of all the spins in the particle.

For a description of ferrofluids, see "Magnetic Fluids" by S. E. Khalafalla in *Chem. Tech.*, page 540, September, 1975; and "Some Applications of Ferrofluid Magnetic Colloids", by Kaiser and Miskolczy *IEEE Transactions on Magnetics*, page 694, volume MAG-6 No. 3 September, 1970.

Generally speaking, magnetic material can exhibit three modes of magnetic behavior depending on particle size. Superparamagnetic behavior, one of the three modes, is exhibited by different materials at particles sizes which vary with the identity of the material. A simplified relationship which allows an approximation for determining the maximum particle diameter at which a given material will exhibit superparamagnetism is given by the equation "Critical volume = $25kT \div K$" where $k$ is Boltzmann's constant ($1.38 \times 10^{-16}$ erg/degree), $T$ is the Kelvin temperature, and $K$ is the magnetic anisotropy in erg/cubic centimeter. This equation is an approximation for spherical uniaxial particles of equal size. The anisotropy values for K are related to the measureable anisotropy constants $K_1$ and $K_2$ by: $K = K_1/4$ when $K_1$ is greater than 0; and $K = K_1/12 + K_2/27$ when $K_1$ is less than 0. For example, add to $T = 298°$ Kelvin, the maximum diameters for superparamagnetic behavior in spherical particles of iron, cobalt, and magnetite are respectively: 250 angstroms, 120 angstroms, and 600 angstroms. For a more thorough discussion of superparamagnitism, see "Superparamagnetism" by C. P. Bean and J. D. Livingston, *J Appl Phys*, supplement to volume 30, no. 4, page 1205 (1959).

Typical suitable ferrofluids for use in accordance with the practice of the present invention may be prepared by ball-milling the magnetic particles for periods of about 1,000 hours in the presence of a surfactant as disclosed in "Magnetic Properties of Stable Dispersions of Sub-domain Magnetite Particles", *J Appl Phys*, volume 41, page 1064, by R. Kaiser and G. Miskolczy (1970). Residual coarse material may be centrifuged or allowed to settle out in order to produce a stable ferrofluid by this mechanical milling method. Other methods of preparing ferrofluids include chemical precipitation methods. See, for example, "Preparing Magnetic Fluids by a Peptizing Method", U.S. Bureau of Mines Technical Progress Report 59, G. W. Reimers and S. E. Khalafalla, September, 1972; and U.S. Pat. No. 3,228,881 to Thomas directed to a method of preparing a dispersion of discrete particles of ferromagnetic metals.

Commercially available ferrofluids, such as, for example, ferrofluids exhibiting superparamagnetic behavior can be employed in the practice of the present invention. Such ferrofluids are commercially available from Ferrofluidics Corporation of Burlington, Mass.

Once the superparamagnetic fluid has been prepared, by whatever method, or obtained commercially, metal flakes are added thereto, and, optionally, an appropriate diluent is added. By "appropriate diluent" it is meant that the diluent is compatible with the carrier liquid used in making the ferrofluid; for example, if the ferrofluid is water based, the diluent is water. Similarly, if the ferrofluid is hydrocarbon based, the diluent is a hydrocarbon liquid.

The metal flakes to be added to the ferrofluids can comprise any size flakes which will remain suspended in the ferrofluid and not settle out under conditions of use. In this regard, metal flakes of a size of about 325 L mesh or smaller in size than about 325 L mesh is preferred. However, larger size flakes can be employed provided they do not settle out of the ferrofluid. Metals of good reflectivity are preferred in the practice of the present invention since it is the reflection of light from the broad surface area of the flakes which provides contrast between magnetic field aligned portions of the composition and non-aligned portions of the composition. In this regard, aluminum flakes available from Aluminum Corporation of America have been found to provide excellent results when used in the practice of the present invention. However, any metal flake can be employed which provides an optical characteristic in alignment which is visibly distinguishable from that presented by the flake when viewed on edge or on end.

It has been found that metal flakes suspended in ferrofluids will become aligned in the direction of the magnetic field to which they are subjected and that, furthermore, the alignment is such that predominantly the broad surface area of the metal flake aligns parallel to the magnetic field direction to which the composition is subjected. While the mechanism which accounts for this alignment of the metal flake in a ferrofluid which is subjected to a magnetic field is unknown, it is believed that a guest-host interaction is involved. That is, it is believed that the formation of chains by the magnetic particles in the ferrofluid when subjected to a magnetic field causes the metal flakes suspended in the ferrofluid to align with the chain formation.

While preferred ranges of ferrofluid, diluent and metal flakes are presented in the examples set forth below, it will be appreciated that amounts of components outside these ranges can be employed. For example, in the examples presented below, the magnetic field was varied between 0.5 gauss and 300 gauss. The designation "too thick" and "too thin" in the examples set forth below indicate that satisfactory optical contrast was not achieved with a magnetic field between about 0.5 gauss and about 300 gauss. In the case of a designation "too thick" a magnetic field greater than about 300 gauss should be employed. Where the designation "too thin" appears, it indicates that for the relatively small planer sample tested, the amount of aluminum flakes contained in the sample did not give satisfactory optical contrast. A larger area display should provide results which are exactable to low resolution imaging requirements.

The following examples are set forth to illustrate both preferred embodiments of the present invention and to give guidance to one skilled in the art as to the relative compositional values which are satisfactory for relatively low magnetic field strength imaging; i.e., magnetic field strengths between about 0.5 gauss to about 300 gauss. These examples are given as illustrated but not limiting examples of the present invention. In all cases, unless otherwise noted, the ferrofluids were obtained from Ferrofluidics Corporation of Burlington, Massachusetts and had a magnetic saturation of about 200 gauss; the hydrocarbons liquid diluent was SOHIO produce 3440 commercially avaiable from Standard Oil Company of Ohio; the metal flakes were aluminum flakes of a size which permits passage through a 325 mesh screen, commercially available from Alcoa and parts and percentages are by weight.

EXAMPLE I

A water based composition comprising one part (10%) water based ferrofluid; one part (10%) metal flakes; and, eight parts (80%) water is made by adding the flakes and water to the ferrofluid and stirring to achieve a resulting composition of uniform apearance. The composition is placed between an about four micron thick piece of Mylar film and a glass microscope slide to form a magneto-optic cell. The cell is subjected to a magnetic field which is varied between about 0.5 gauss and about 300 gauss.

Prior to being subjected to the magnetic field, the cell appears dark black. Upon being subjected to the field, the metal flakes impart an an aluminum appearance to portions of the cell subjected to the magnetic field.

The remaining hydrocarbon based ferrofluid examples are performed in the manner of Example I. The compositional values and results are set forth in Table I, below. *"D" means diluent, *"FF" means ferrofluid and *"MF" means metal flakes. In each example, the result is based on a magnetic field varied between about 0.5 gauss and about 300 gauss.

TABLE I

| EXAMPLE I | Parts *D | Parts *FF | Parts *MF | Result |
|---|---|---|---|---|
| II | 0 | 1(50%) | 1(50%) | Too Thick |
| III | 10 (83%) | 1(8 ⅓%) | 1(8 ⅓%) | O.K. |
| IV | 20 (91%) | 1(4 ½%) | 1(4 ½%) | O.K. |
| V | 50 (96%) | 1(2%) | 1(2%) | O.K. |
| VI | 100 (98%) | 1(1%) | 1(1%) | Too Thin |
| VII | 0 | 1(33%) | 2(67%) | Too Thick |
| VIII | 20 (87%) | 1(4 ⅓%) | 2(8 ⅔%) | Too Thick |
| IX | 40 (93%) | 1(2%) | 2(5%) | O.K. |
| X | 100 (97%) | 1(1%) | 2(2%) | O.K. |
| XI | 200 (98.5%) | 1(.5%) | 2(1%) | O.K. |
| XII | 0 | 1(20%) | 4(80%) | Too Thick |
| XIII | 10 (67%) | 1(6.6%) | 4(26.4%) | Too Thick |

TABLE I-continued

| EXAMPLE I | Parts *D | Parts *FF | Parts *MF | Result |
|---|---|---|---|---|
| XIV | 20 (80%) | 1(4%) | 4(16%) | Marginally O.K. |
| XV | 50 (91%) | 1(1.8%) | 4(7.2%) | O.K. |
| XVI | 100 (95%) | 1(1%) | 4(4%) | O.K. |

It is to be noted that the above results were obtained with magnetic fields applied between about 0.5 gauss and about 300 gauss. Accordingly, magnetic fields greater than about 300 L gauss would have to be employed or, in the alternative compositional variations beyond Table I would have to be employed to obtain satisfactory optical results. For example, as noted in Table I that in examples II, VII, and XII, the resulting composition was too thick to provide satisfactory optical characteristics. In these examples, no diluent was added to the ferrofluid-metal flake composition and the ferrofluid was always present in an amount no greater than an equal part by weight of the metal flakes. The thickness of the resulting composition in those three examples can be altered by varying the ratio of ferrofluid to metal flakes such that the ferrofluid is always present in a greater amount by weight than the metal flakes. In this manner, suitable optical response can be obtained for magnetic fields between about 0.5 gauss and about 300 gauss. It is to be noted that as earlier defined, a ferrofluid contains a liquid carrier in which the superparamagnetic particles are colloidally suspended. Accordingly, the addition of greater amounts of ferrofluid relative to metal flakes will inherently dilute the resulting composition. As a matter of preference, the addition of diluent is preferred rather than the use of more ferrofluid simply as a matter of practical economics.

While this invention has been described with respect to particularly preferred embodiments of the composition, it would be appreciated by those skilled in the art that the invention is not limited thereto. Furthermore, the novel imaging composition of the present invention finds utility in a number of applications. For example, it can be used as a liquid developer for latent magnetic images; and among other uses, can be utilized in a latent magnetic image reader such as one described in the backgrond section of this application.

What is claimed is:

1. An imaging composition consisting essentially of a ferrofluid and metal flakes, said metal flakes being detached from magnetic particles suspended in said ferrofluid and capable of being aligned in the direction of a magnetic field to which said ferrofluid is subjected.

2. The composition of claim 1 further including a diluent.

3. The composition of claim 2 comprising by weight from about 80% to about 98.5% diluent, from about 0.5% to about 8.5% ferrofluid, and from about 1% to about 16% metal flakes.

4. The composition of claim 2 wherein said diluent comprises water.

5. The composition of claim 4 wherein by weight said ferrofluid comprises about 10% and said metal flakes comprise about 10% of said composition.

6. The composition of claim 3 wherein said diluent comprises a hydrocarbon liquid.

7. The composition of claim 6 wherein by weight said composition comprises about one part ferrofluid, about one part metal flakes and from about 10 to about 50 parts diluent.

8. The composition of claim 6 wherein by weight said composition comprises about one part ferrofluid, about two parts metal flakes and from about 40 to about 200 parts diluent.

9. The composition of claim 6 wherein by weight said composition comprises about one part ferrofluid, about four parts metal flakes and from about 40 to about 200 parts diluent.

* * * * *